(12) United States Patent  
Yamada

(10) Patent No.: US 7,662,188 B2  
(45) Date of Patent: Feb. 16, 2010

(54) INTERNAL SINUS MANIPULATION (ISM) PROCEDURE FOR FACILITATING SINUS FLOOR AUGMENTATION IN DENTAL PROCEDURES

(76) Inventor: Jason M. Yamada, 29 Quarter Horse La., Rolling Hills Estates, CA (US) 90274

( * ) Notice: Subject to any disclaimer, the term of this patent is extended or adjusted under 35 U.S.C. 154(b) by 240 days.

(21) Appl. No.: 11/895,823

(22) Filed: Aug. 28, 2007

(65) Prior Publication Data

US 2008/0161934 A1    Jul. 3, 2008

Related U.S. Application Data

(60) Provisional application No. 60/882,940, filed on Dec. 31, 2006.

(51) Int. Cl.
*A61F 2/02* (2006.01)
*A61B 19/00* (2006.01)

(52) U.S. Cl. .................. 623/17.17; 128/898; 433/172; 606/191

(58) Field of Classification Search .............. 606/199, 606/93, 191; 623/17.17
See application file for complete search history.

(56) References Cited

U.S. PATENT DOCUMENTS

| | | | | |
|---|---|---|---|---|
| 5,711,315 | A * | 1/1998 | Jerusalmy | 128/898 |
| 6,206,698 | B1 * | 3/2001 | Billingsley | 433/164 |
| 6,799,970 | B2 * | 10/2004 | Martin et al. | 433/173 |
| 7,125,253 | B2 * | 10/2006 | Kitamura et al. | 433/173 |
| 2005/0136377 | A1 * | 6/2005 | Corti | 433/144 |
| 2006/0084034 | A1 * | 4/2006 | Hochman | 433/173 |

* cited by examiner

*Primary Examiner*—Bruce E Snow
*Assistant Examiner*—Melissa Montano
(74) *Attorney, Agent, or Firm*—Robert R. Meads

(57) ABSTRACT

An internal sinus manipulation procedure for augmenting bone of a dental patient between the floor of the patient's sinus and a raised portion of the patient's sinus membrane comprising exposing a portion of the patient's sinus membrane immediately adjacent the floor of the patient's sinus followed by (i) a simultaneous and controlled lifting and lateral separation of the exposed portion of the sinus membrane from the sinus floor to form an open pocket between the sinus membrane and the sinus floor, (ii) introduction of a bone grafting material into the pocket and (iii) a compacting of the bone grafting material.

5 Claims, 5 Drawing Sheets

INTERNAL SINUS MANIPULATION (ISM) PROCEDURE FOR FACILITATING SINUS FLOOR AUGMENTATION IN DENTAL PROCEDURES

RELATED PATENT APPLICATION

The present application claims the benefit of U.S. Provisional Patent application Ser. No. 60/882,940 filed Dec. 31, 2006, which is herein incorporated by reference.

BACKGROUND OF INVENTION

The human posterior maxilla often presents dental clinicians with situations where there is a need to increase the available bone between the schneiderian (sinus) membrane and the floor of the maxillary antrum. For example, because of inadequate bone in the posterior maxilla of some dental patients, augmentation of the sinus floor is required before placement of a dental implant.

An early sinus augmentation technique was presented by H. Tatum Jr. in 1977, later published in "Maxillary and Sinus Implant Reconstructions", Dent Clin North Am 1986; 30(2): 207-229 and first described by P. J. Boyne and R. A. James in 1980, "Grafting of the Maxillary Sinus Floor With Autogenous Marrow and Bone" J Oral Surg 1980; 38(8): 613-616.

Originally Tatum accessed the maxillary sinus through the alveolar ridge crest using various instruments of his own design. Boyne and James later developed a lateral window technique modifying the known Caldwell-Luc procedure. In the Boyne and James technique, a horizontal incision was made in the posterior maxillary vestibule followed by exposure of the lateral osseous ridge wall of the posterior maxilla. An osteotomy window was then created by using burs in the lateral osseous ridge wall. The window of lateral wall was either removed or medially repositioned. The sinus membrane was gently released and reflected upward and an autogenous bone graft was then inserted over the exposed sinus floor. The flap was then replaced and primarily closed. A bladed-type implant was placed at 10-12 weeks following the augmentation procedure.

These fundamental concepts have been retained in contemporary lateral window techniques such as described by C. E. Misch in "Maxillary Sinus Augmentation For Endosteal Implants: Organized Alternative Treatment Plans" Int J Oral Implant 1989: 4:49-58 and by J. N. Garg and C. R. Quinones in "Augmentation of the Maxillary Sinus. A Surgical Technique" Pract Periodontics Aesthet Dent 1997; 9:211-219.

Implants are now often placed at the time of grafting according to the amount of pre-existing bone available for initial stability. However, post-operative complications such as pain or swelling due to extensive surgical trauma may increase patient discomfort.

In 1994, Summers published a method for the sinus augmentation using an osteotome instrument, R. B. Summers "A New Concept In Maxillary Sinus. A surgical Technique" Compendium 1994: 15(2):152-158 and "The Osteotome Technique: Part 3-Less Invasive Methods Of Elevating The Sinus Floor" Compendium 1994: 15(6):698-704. In the Summers technique, after initial implant osteotomy drilling was performed, approximating the sinus floor, an osteotome was inserted to the osteotomy site and gently tapped fracturing and moving the sinus floor superiorly. The fractured sinus bone was pushed up, reflecting the Schneiderian membrane, and various bone graft materials were then added and implants immediately placed.

Recently, modifications of the Summer's technique using spreading and condensing instrumentation and elevating the sinus using various pressure techniques have also been reported. Bori J E. "A new sinus lift procedure: SA-4/'O'". Dent Implantol Update 1991; 2(4):33-37; Smiler D G. "The sinus lift graft: basic technique and variations". Pract Periodontics Aesthet Dent 1997; 9(8):885-893.9; Bruschi G B, Scipioni A, Calesini G, Bruschi E. "Localized management of sinus floor with simultaneous implant placement: a clinical report" Int J Oral Maxillofac Implants 1998; 13(2):219-226; M. Toffler "Site development in the posterior maxilla using osteocompression and apical alveolar displacement" Compend Contin Educ Dent 2001; 22(9):775-784; P. A. Fugazzotto, P. S. De "Sinus floor augmentation at the time of maxillary molar extraction: success and failure rates of 137 implants in function for up to 3 years", J Periodontol 2002; 73(1):39-44; A. A. Winter A. S. Pollack, R. B Odrich "Placement of implants in the severely atrophic posterior maxilla using localized management of the sinus floor: a preliminary study". Int J Oral Maxillofac Implants 2002; 17(5):687-695; M. Soltan, D. G. Smiler "Antral membrane balloon elevation". J Oral Implantol 2005; 31(2):85-90; L. Chen, J. Cha "An 8-year retrospective study: 1,100 patients receiving 1,557 implants using the minimally invasive hydraulic sinus condensing technique". J Periodontol 2005; 76(3):482-491.

However, the amount of augmentation of the sinus floor and the volume of bone created is limited using the foregoing techniques and it is reportedly difficult in many cases to control the osteotome tapping force in order to produce effective membrane lifting without membrane perforation and on occasion the tapping procedure to fracture the sinus floor or to add bone graft material causes discomfort to the patient during the surgery.

A new minimally invasive sinus augmentation technique is presented herein, called the "Internal Sinus Manipulation (ISM)" procedure, and is designed to facilitate sinus floor augmentation predictably while reducing treatment morbidity.

SUMMARY OF INVENTION

The ISM internal sinus manipulation procedure augments bone of a dental patient between the floor of the patient's sinus and a raised portion of the patient's sinus membrane. Basically the ISM procedure comprises exposing a portion of the patient's sinus membrane immediately adjacent the floor of the patient's sinus followed by (i) a simultaneous and controlled lifting and lateral separation of the exposed portion of the sinus membrane from the sinus floor to form an open pocket between the sinus membrane and the sinus floor, (ii) introduction of a bone grafting material into the pocket and (iii) a compacting of the bone grafting material.

The exposing of the portion of the sinus membrane should be without perforation of the sinus membrane and may be accomplished by the use of standard drills and drilling techniques and the like controlled to create an upward channel in the bone of the patient within the maxillary posterior area where the patient's existing bone is not sufficient. In this regard, the upper end of the channel should extend to the base of the sinus floor and should be small enough to only expose the portion of the sinus membrane that is to be lifted and laterally extended to form the pocket.

The simultaneous lifting and lateral separation of the portion of sinus membrane from the sinus floor may be accomplished using a sinus lifting tool that includes a disk-shaped tip and an angled neck. The disk-shaped tip is designed to release the sinus membrane from the bony wall of sinus floor.

The angled neck is designed to aid in the proper positioning of the working tip. An inflection portion of the angled neck extending from the working tip allows the clinician to feel the tension of the sinus membrane and to determine the amount of initial lateral and vertical membrane reflection. The procedure for membrane release and elevation should be continued until a planned amount of sinus extension is achieved and the pocket is defined.

The packing of the bone grafting material may be accomplished with standard tapping burs or the like. Preferably however, prior to such tapping, a bone material condensing tool having longitudinally extending handle carrying at its distal end a laterally extending bone condensing head having a concave upper surface is employed to pre-condense the bone packing material upon a spinning of the handle of the tool on its longitudinal axis such that the condensing head produces a mixing and condensing of the bone packing material within the pocket.

Also, in the ISM procedure, if the exposing of the portion of the sinus membrane leaves fragments of bone extending laterally into the channel adjacent the opening into the pocket, a bone breaking tool or instrument including a longitudinally extending handle having a laterally extending distal head with an inwardly and upwardly inclined lower surface may be employed to hook and break off such bone fragments leaving a clear opening into the pocket for the membrane lifting tool as illustrated in the accompanying drawings.

BRIEF DESCRIPTION OF ACCOMPANYING DRAWINGS

Figure 1:
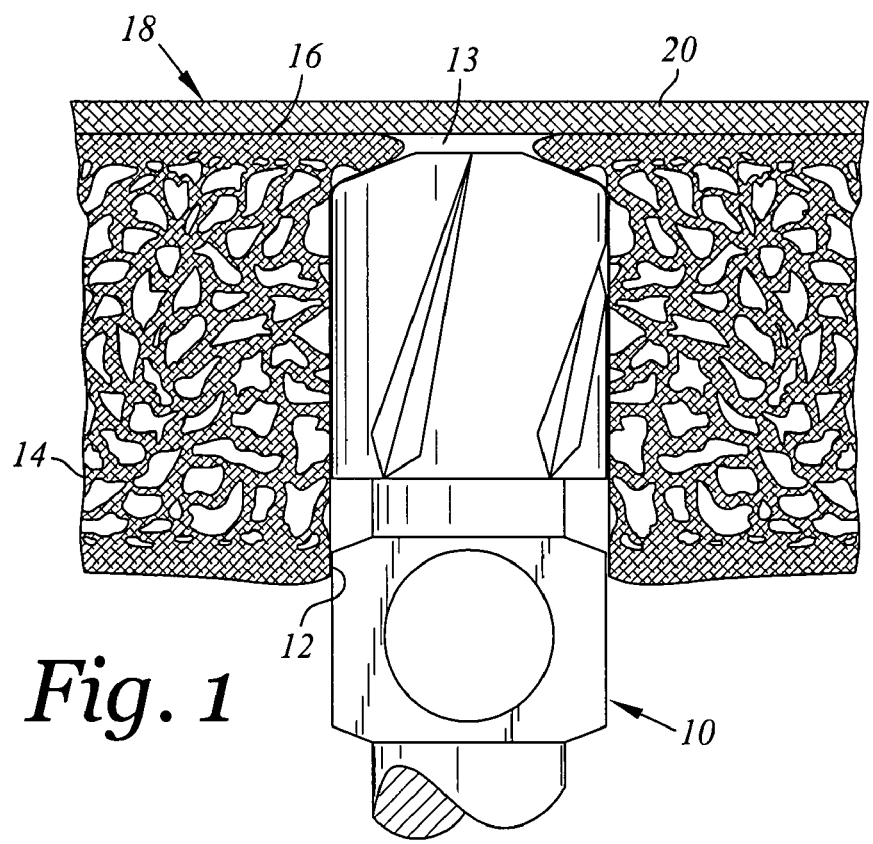
FIG. 1 is a fragmentary sectional side view illustrating the step of exposing a portion of a sinus membrane as by employing a standard drill to form an upward channel through bone in the maxillary posterior area of a patent where the bone is of insufficient thickness to effectively receive a dental implant.
Figure 3:
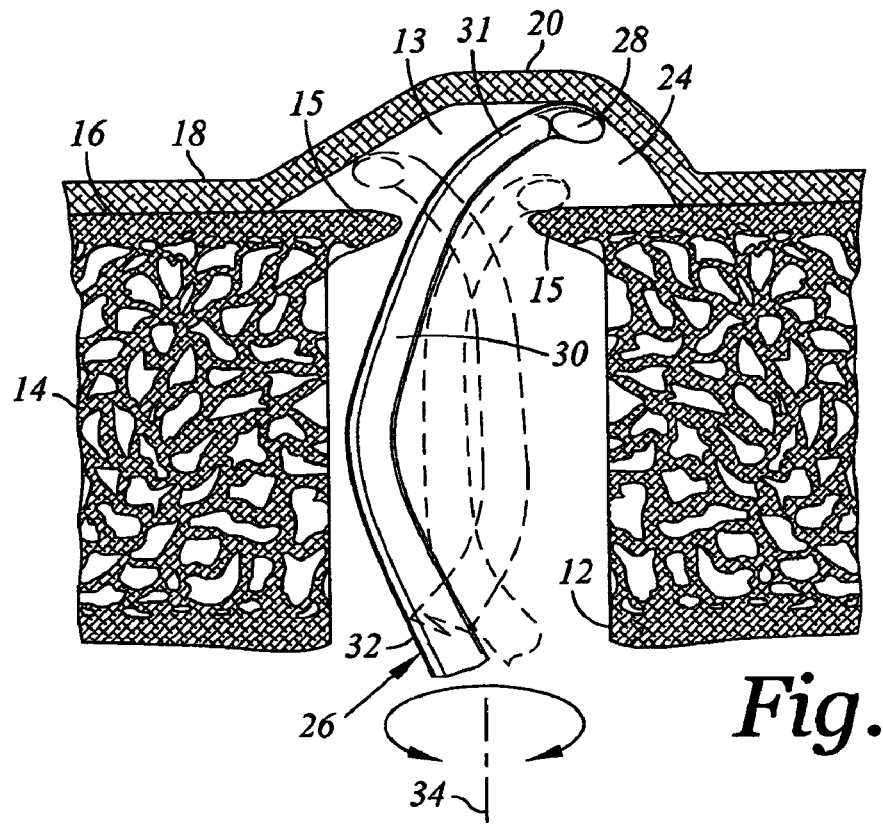

FIG. 3 is a fragmentary sectional side view of the bone channel of FIG. 1 receiving a sinus-lifting tool that includes a disk-shaped tip and an angled neck simultaneously lifting and laterally separating the exposed portion of the sinus membrane from the sinus floor to form a relatively small pocket between the sinus membrane and the sinus floor with lateral movement and a turning of the sinus lifting tool about a vertically extending axis of rotation.

Figure 4:
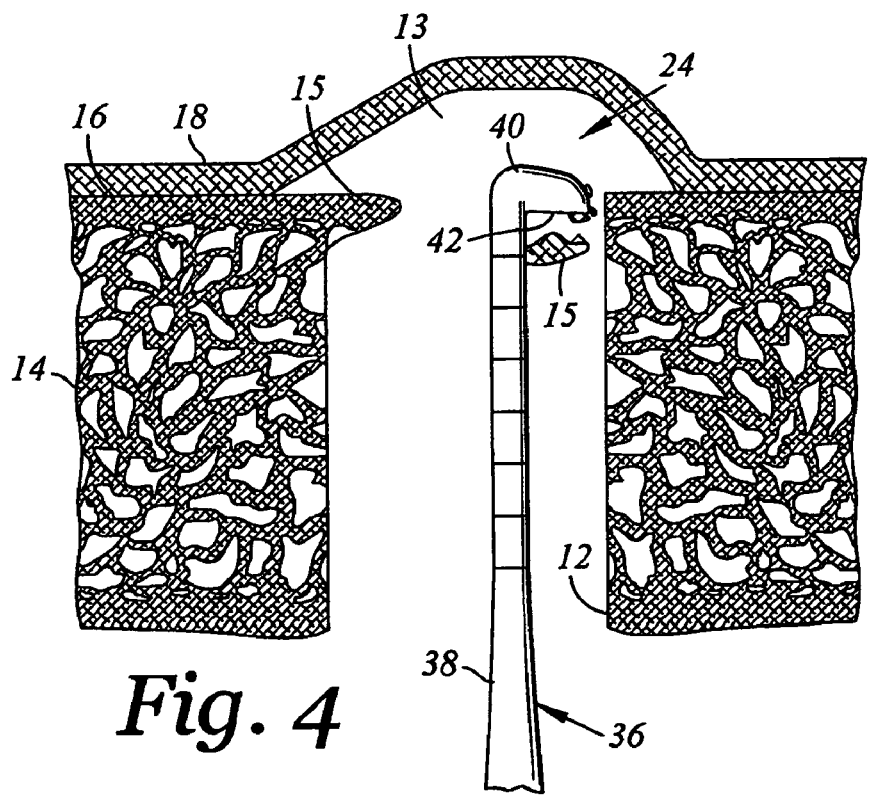
Figure 5:
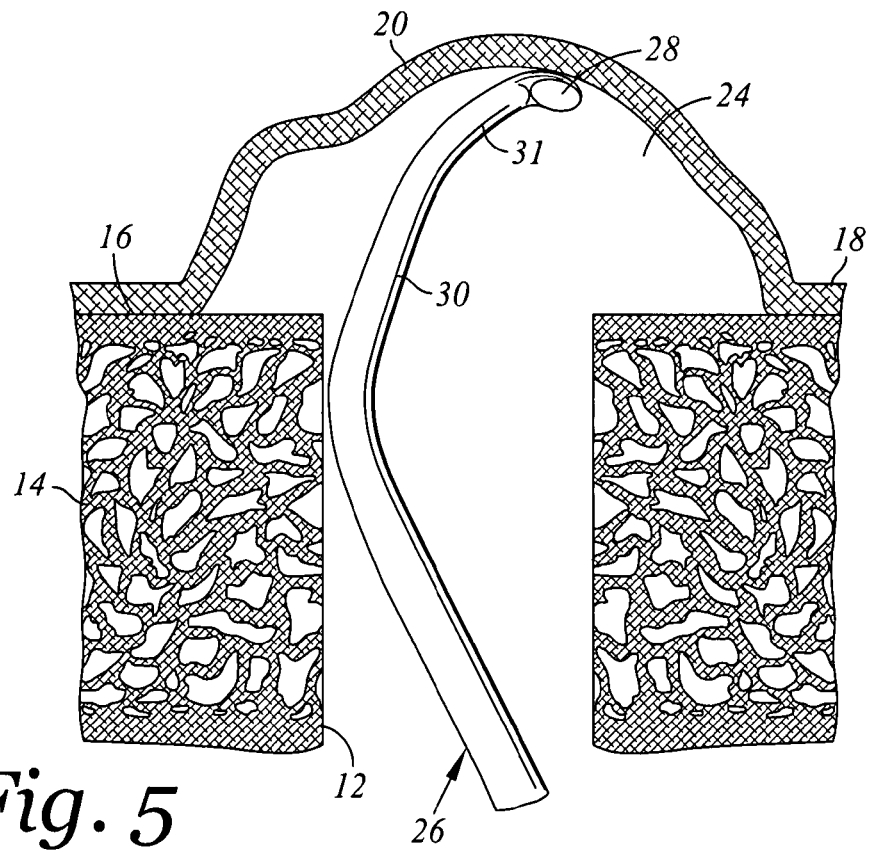

FIG. 4 is a fragmentary sectional side view of the bone channel of FIG. 3 receiving a bone breaking tool or instrument including a longitudinally extending handle having a laterally extending distal head with an inwardly and upwardly inclined lower surface employed to hook and break off bone fragments extending into the upper open end of the channel leaving a clear opening into the pocket for the membrane lifting tool as illustrated in FIG. 5.

FIG. 5 is a fragmentary sectional side view of the bone channel of FIG. 4 again receiving the sinus-lifting tool of FIG. 3 to simultaneously further lift and laterally separate the exposed portion of the sinus membrane from the sinus floor to enlarge the pocket between the sinus membrane and the sinus floor with lateral movement and a turning of the sinus lifting tool about a vertically extending axis of rotation as shown in FIG. 3.

Figure 6:
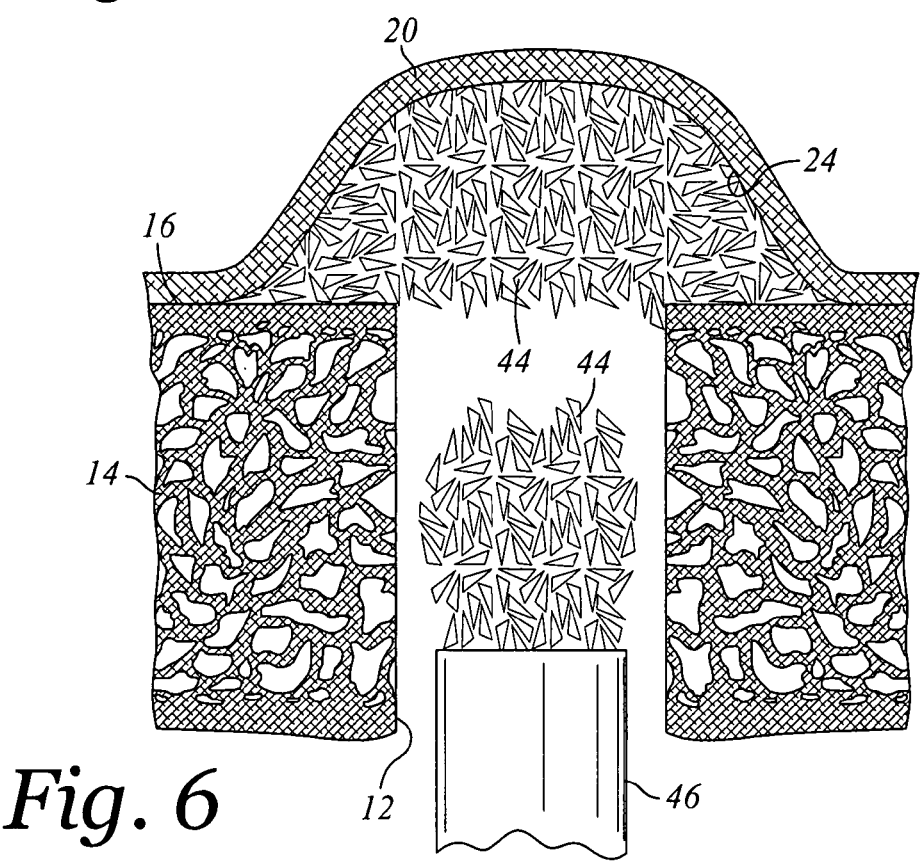

FIG. 6 is a fragmentary sectional side view of the channel and pocket of FIG. 5 illustrating the introduction of bone grafting material into the enlarged pocket using a graft material insertion tool, the graft material in the pocket slightly enlarging the pocket to a relatively smooth dome shape.

Figure 7:
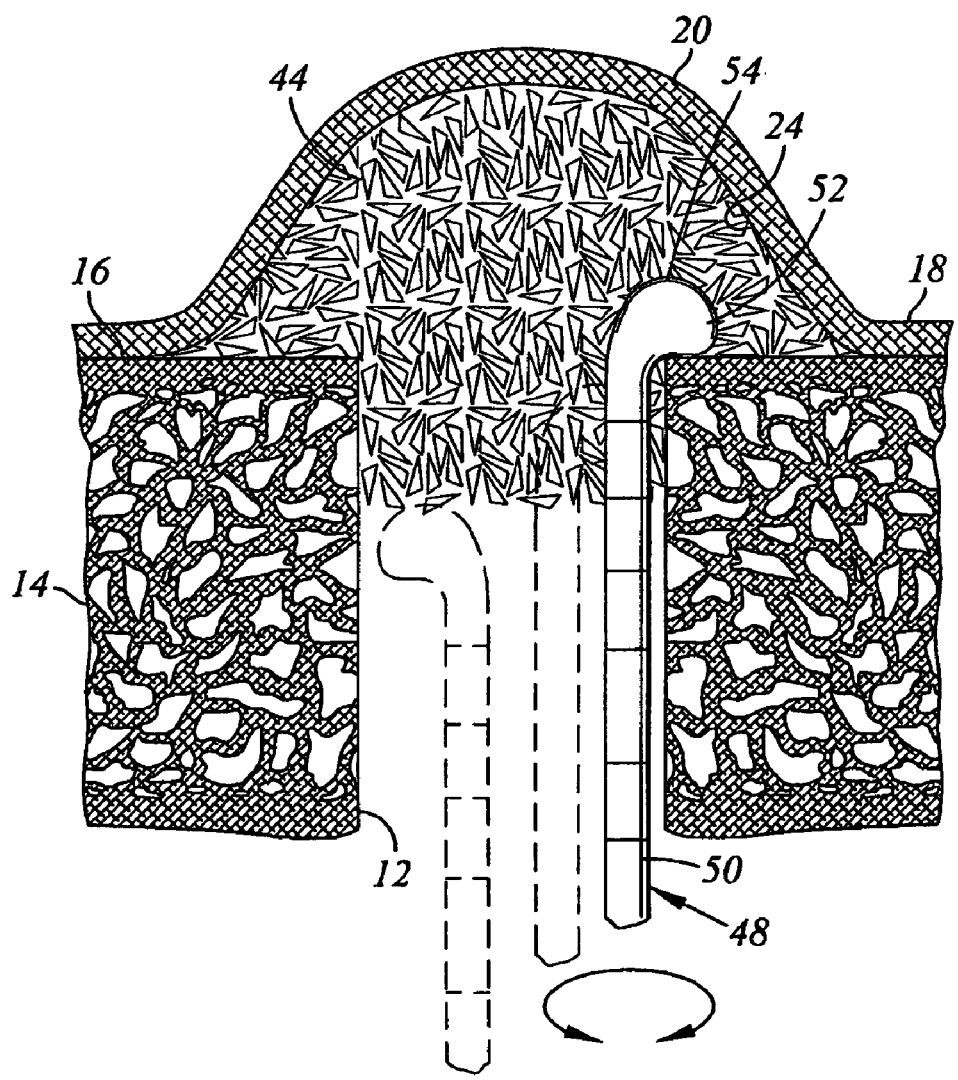

FIG. 7 is a fragmentary sectional side view of the channel and pocket of FIG. 6 illustrating a bone material condensing tool having a longitudinally extending handle carrying at its distal end a laterally extending bone condensing head having a concave upper surface employed to pre-condense the bone packing material upon a spinning of the handle of the tool on its longitudinal axis such that the condensing head produces a mixing and condensing of the bone packing material within the pocket.

Figure 8:
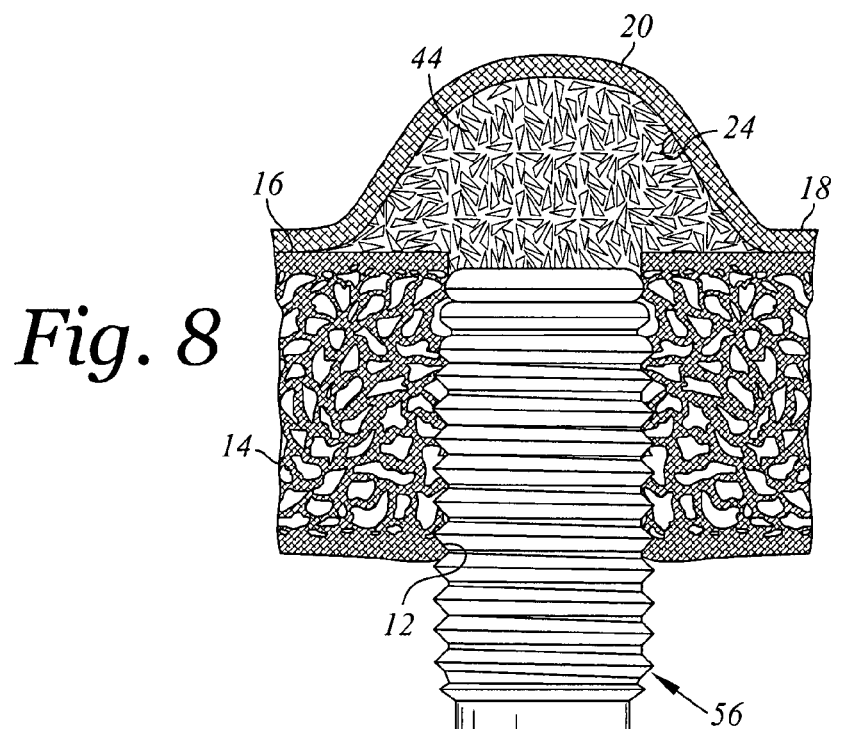

FIG. 8 is a fragmentary sectional side view of the channel and the bone graft material filled pocket of FIG. 7 including a standard tapping bur for further condensing the bone graft material.

Figure 9:
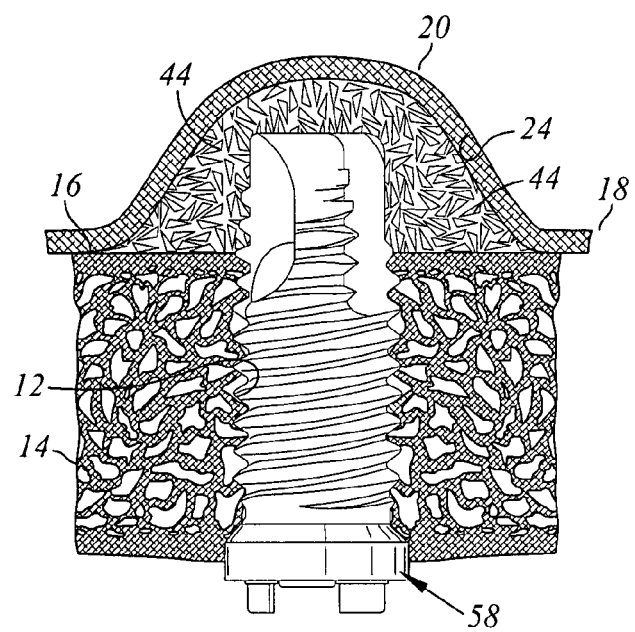

FIG. 9 is a fragmentary sectional side view of the channel and the condensed bone graft material of FIG. 8 including a dental implant recurred in the bone and condensed bone graft material.

DETAILED DESCRIPTION OF INVENTION

In practice, prior to beginning the ISM procedure generally described above, a patient treatment plan should be established based on clinical evaluation, diagnostic wax-up on a study cast and radiographic information from a periapical radiograph, a panoramic radiograph or a computerized tomogram. Then, after full thickness flap elevation or through a flapless procedure, a standard implant osteotomy drilling sequence is followed using a surgical guide, a round marker and subsequent twist drills. Such a drilling procedure is depicted in FIG. 1 where a standard twist drill 10 is shown forming a channel 12 in the bone 14 of in the maxillary posterior area of a patent where the bone is of insufficient thickness to effectively receive a dental implant. As previously indicated, conventional twist drills or surgical round diamond burs can be used to drill up to the sinus floor 16, barely breaking through the existing bone, without perforating the sinus membrane 18, to expose through an upper open end 13 of the channel 12, the portion 20 of the sinus membrane that is to be lifted and laterally separated from the sinus floor 16 in the ISM procedure.

Figure 2:
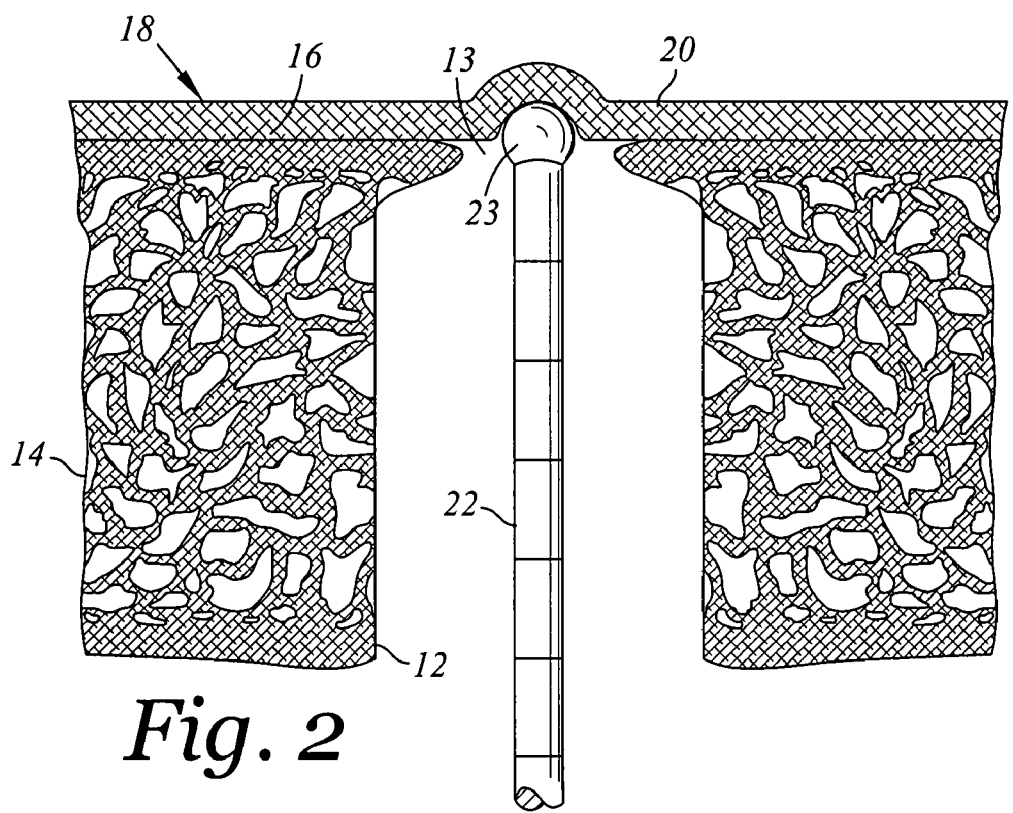
FIG. 2 is a fragmentary sectional side view showing the bone channel of FIG. 1 receiving a standard depth-measuring instrument for determining the depth of the bone surrounding the channel.

Following the formation of the bone channel 12 as depicted in FIG. 1 and as shown in FIG. 2, a conventional depth gauge instrument 22 having axially spaced measuring marks and a blunt tip 23 may be employed to measure the thickness of the bone 14 in the channel 12, check the integrity of membrane 18, particularly of portion 20, and to verify the amount of the membrane lifting previously determined in the development of the patient treatment plan.

Next, as illustrated in FIG. 3, the portion 20 of the sinus membrane 18 is simultaneously lifted and laterally separated from the sinus floor 16 to form a small downwardly open pocket 24 between the vertically lifted portion 20 of the sinus membrane 18 and the sinus floor 16. Preferably, such simultaneous lifting and lateral separation is accomplished by the use of a sinus lifting tool 26 that includes a disk-shaped tip 28 and an angled neck 30 extending longitudinally from a handle portion 32. The disk-shaped tip 28 is designed to release the sinus membrane 18 from the bony wall of sinus floor 16. The angled neck 30 is designed to aid in the proper positioning of the working tip 28. An inflection portion 31 of the angle of the neck 30 extending from the working tip 28 allows the clinician to feel the tension of the sinus membrane 18 and to determine the amount of initial lateral and vertical membrane reflection. As illustrated in FIG. 3 by the solid, dashed and broken line outlines of the tool 26, in the formation of the pocket 24 the tool 26 is simultaneously raised and turned back and forth on vertically extending axis 34 with the tip 28 simultaneously lifting and laterally separating the membrane 20 from the sinus floor 16 to form and enlarge the pocket 24. This procedure of simultaneous membrane lateral release and elevation is continued until a planned amount of sinus extension is achieved and the small open pocket 24 is defined. A preferred form of the tool 26 is described and illustrated more fully in the concurrently filed U.S. patent application Ser. No. 11/895,811, entitled "Improved Sinus Membrane Lifting and Lateral Separation Instrument" published Jul. 3, 2008 as Pub. No.: US2008/01618456A1), incorporated herein by this reference.

As illustrated in FIGS. 1-4, in the formation of the channel 12, small inwardly directed bone fragments 15 may surround or extend into the small opening 13 in the channel 12. As illustrated in FIG. 4, after the formation of the small pocket 24 as shown in FIG. 3, such bone fragments 15 are removed. Preferably such bone fragment removal is accomplished using a bone breaking tool or instrument 36 including a longitudinally extending handle 38 having a laterally extending distal head 40 with an inwardly and upwardly inclined lower surface 42. As illustrated, the lower surface 42 is employed to hook the bone fragments 15 and with a downward pulling on the handle 38 to break off the bone fragments 15 extending into the upper open end 13 of the channel 12 leaving a clear opening into the pocket 24 for the membrane lifting tool 26 as illustrated in FIG. 5. A preferred form of the tool 36 is described and illustrated more fully in the concurrently filed U.S. patent application Ser. No. 11/895,810, entitled "Improved Bone Breaking Instrument" Published Jul. 3, 2008 as Pub. No.: US2008/0151828A 1), incorporated herein by this reference.

While not specifically shown, if it is desired to further refine the open end 13 or inner wall of the channel before proceeding further with the ISM procedure, the channel 12 may be widened, for example, to the appropriate width of any subsequently planned implant placement utilizing the same length of stopping cylinder twist drills or standard implant twist drills as depicted in FIG. 1.

As shown in FIG. 5, following the removal of the inwardly directed fragments from the channel 12 as shown in FIG. 4 or the above mentioned widening of the channel 12, the previously described sinus-lifting tool 26 of FIG. 3 is again inserted into the bone channel 12 to simultaneously further lift and laterally separate the exposed portion 20 of the sinus membrane 18 from the sinus floor 16 to enlarge the pocket 24 between the sinus membrane 18 and the sinus floor with a turning of the sinus lifting tool about a vertically extending axis of rotation as shown in FIG. 3.

Next, as depicted in FIG. 6, an appropriate standard bone grafting material 44 is introduced into the enlarged pocket 24 using a graft material insertion tool 46 designed to carry the material upward in the channel and into the pocket, the graft material in the pocket slightly enlarging the pocket to a relatively smooth dome shape.

The bone graft material 44 in the enlarged pocket 24 shown in FIG. 7 is then condensed by a bone material condensing tool 48 having longitudinally extending handle 50 carrying at its distal end a laterally extending bone condensing head 52 having a concave upper surface 54 employed to pre-condense the bone packing material upon a spinning of the handle 50 of the tool on its longitudinal axis and lateral movement (depicted by the dashed outlines) of the tool such that the condensing head produces a mixing and condensing of the bone packing material within the pocket 24. A preferred form of the tool 48 is described and illustrated more fully in the concur-rently filed U.S. patent application Ser. No. 11/895,812, entitled "Improved Bone Graft Material Packing Instrument" (published Jul. 3, 2008 as Pub. No.: US 2008/0161819 A1) incorporated herein by this reference.

At the final stage of bone grafting, a conventional tapping bur 56 can be used to pack and push up additional bone graft material 44 into the pocket 24 (or osteotomy socket) as depicted in FIG. 8. A conventional depth gauge instrument (not shown) can be used to check the height of the vertical augmentation of the membrane portion 20 while packing the bone material.

After completion of the bone grafting, a conventional dental implant can be placed in the bone channel 12 and the packed bone graft material 44 in the pocket 24 in a conventional manner as depicted in FIG. 9.

While particular embodiments of the method and the preferred instruments employed in the method have been illustrated and described in detail above, it is appreciated that changes and modifications may be made in the illustrated embodiments without departing from the spirit of the invention. Accordingly, the scope of present invention is to be limited only by the terms of the following claims.

The invention claimed is:

1. An internal sinus manipulation procedure for augmenting bone of a dental patient between a bony floor of the patient's sinus and a raised portion of the patient's sinus membrane, comprising:

creating an upward channel in bone within a maxillary posterior area of the patient such that an upper end of the channel extends to a base of the bony floor of the sinus and is sized to expose a portion of the patient's sinus membrane over the upper end of the upward channel;

selecting a sinus membrane lifting instrument sized to extend upwardly within the channel and including (i) a longitudinally extending handle (ii) an angled neck extending longitudinally at an upward angle outward from the longitudinally extending handle and (iii) a working tip extending at an upward angle outward from the angled neck and having an upwardly curved upper surface for positioning by the angled neck against the exposed portion of the sinus membrane extending over the upper end of the upper end of the channel;

moving the selected membrane lifting instrument upward into the channel until the angled neck positions the upwardly curved upper surface of the working tip against the exposed portion of the sinus membrane over the upper end of the channel;

while the curved upper surface of the working tip engages the exposed portion of the sinus membrane, laterally moving and turning the instrument on its longitudinal axis allowing the working tip to separate the sinus membrane from the bony floor of the sinus around the upper end of the channel and the curved upper surface of the working tip to simultaneously lift the exposed portion of the sinus membrane and the sinus membrane separated from bony floor of the sinus around the upper end of the channel to form an open pocket between the sinus membrane and the bony floor, followed by a further lateral moving, turning and lifting of the sinus membrane lifting instrument and its working tip within the pocket to enlarge the pocket to a desired size and shape;

introducing a bone grafting material through the upward channel into the enlarged pocket; and compacting of the bone grafting material within the enlarged pocket.

2. The procedure of claim 1 wherein:

the selecting of the sinus membrane lifting instrument includes selecting an instrument including an inflection portion connecting the angled neck to the working tip that is designed to allow a clinician using the instrument to feel tension in the sinus membrane as the working tip engages the sinus membrane;

the moving of the lifting instrument upward into the channel is until the angled neck and the inflection portion position the upwardly curved upper surface of the working tip against the exposed portion of the sinus membrane over the upper end of the channel; and while the curved upper surface of the working tip is engaging the exposed portion of the sinus membrane, sensing the tension in the sinus membrane while laterally moving, lifting and turning the lifting instrument back and forth on its longitudinal axis.

3. The procedure of claim 1 wherein:

the selecting of the sinus membrane lifting instrument includes selecting an instrument including a working tip having a flat bottom surface;

the moving of the lifting instrument upward into the channel positions the flat bottom surface of the working tip adjacent the bony floor of the sinus; and the lateral moving and turning of the lifting instrument back and forth on its longitudinal axis allows the flat bottom surface of the working tip to separate the sinus membrane from the bony floor of the sinus around the upper end of the channel.

4. The method of claim 1 wherein the compacting of the bone grafting material comprises:

selecting a bone grafting material lateral condensing instrument having a longitudinally extending handle carrying at its distal end a laterally extending head having a concave upper surface;

positioning the condensing instrument upward in the channel with the head of the instrument extending into the bone grafting material; and turning of the handle of the condensing instrument on its longitudinal axis such that the head produces a mixing and circular lateral condensing of the bone grafting material within the pocket.

5. The method of claim 1 wherein any fragment of bone extending laterally into the channel adjacent the opening into the pocket is removed prior to the enlarging of the pocket to its desired size by:

removing the sinus lifting instrument from the channel;

selecting a bone breaking instrument including a longitudinally extending handle having a laterally extending distal head with an inwardly and upwardly inclined lower surface;

positioning the bone breaking instrument upward within the channel with the distal head extending into the pocket and with the inwardly and upwardly inclined lower surface of the distal head hooking onto the fragment of bone;

pulling downward on the handle to break off the bone fragment leaving a clear opening into the pocket;

reintroducing the sinus lifting instrument into channel with the angled neck and working located in the pocket; and resuming the lateral moving, turning and lifting of the instrument with the curved upper surface of the working tip engaging the sinus membrane to enlarge the pocket to its desired size and shape.

\* \* \* \* \*